United States Patent

Bacich et al.

[11] Patent Number: 5,746,692
[45] Date of Patent: May 5, 1998

[54] CATHETER AND ENDOSCOPE SYSTEM WITH DISTAL PROTRUDING BALL TIP AND METHOD

[75] Inventors: Steven R. Bacich, Laguna Niguel; Tuoc Tan Nguyen, Westminster; John Patrick Greelis, Aliso Viego, all of Calif.

[73] Assignee: Imagen Medical, Inc., Laguna Niguel, Calif.

[21] Appl. No.: 630,122

[22] Filed: Apr. 8, 1996

Related U.S. Application Data

[63] Continuation-in-part of Ser. No. 238,314, May 5, 1994, Pat. No. 5,505,686.

[51] Int. Cl.$^6$ .......................................................... A61B 1/00
[52] U.S. Cl. .......................... 600/104; 600/114; 604/280
[58] Field of Search ...................... 600/104, 106, 600/114, 117, 103, 153, 156; 604/280, 164

[56] References Cited

U.S. PATENT DOCUMENTS

| | | |
|---|---|---|
| 3,941,121 | 3/1976 | Olinger et al. . |
| 4,254,762 | 3/1981 | Yoon . |
| 4,345,589 | 8/1982 | Hiltebrandt . |
| 4,345,602 | 8/1982 | Yoshimura et al. . |
| 4,449,532 | 5/1984 | Storz . |
| 4,538,622 | 9/1985 | Samson et al. . |
| 4,545,390 | 10/1985 | Leary . |
| 4,651,751 | 3/1987 | Swendson et al. . |
| 4,682,585 | 7/1987 | Hiltebrandt . |
| 4,762,129 | 8/1988 | Bonzel . |
| 4,773,394 | 9/1988 | Reichstein et al. . |
| 4,793,326 | 12/1988 | Shisido . |
| 4,798,193 | 1/1989 | Giesy et al. . |
| 4,807,593 | 2/1989 | Ito ........................................... 600/114 |
| 4,979,496 | 12/1990 | Komi . |
| 5,025,778 | 6/1991 | Silverstein et al. ....................... 600/104 |
| 5,197,457 | 3/1993 | Adair . |
| 5,207,213 | 5/1993 | Auhll et al. . |
| 5,251,611 | 10/1993 | Zehel et al. . |
| 5,279,280 | 1/1994 | Bacich et al. . |
| 5,292,305 | 3/1994 | Boudewijn et al. . |
| 5,300,023 | 4/1994 | Lowery et al. . |
| 5,337,733 | 8/1994 | Bauerfeind et al. . |
| 5,339,805 | 8/1994 | Parker . |
| 5,356,388 | 10/1994 | Sepetka et al. ....................... 600/280 X |
| 5,390,661 | 2/1995 | Griffith et al. . |
| 5,411,016 | 5/1995 | Kume et al. . |
| 5,490,845 | 2/1996 | Rach .................................... 600/280 X |

OTHER PUBLICATIONS

The Wilkerson Group, Inc., An Assessment of Percutaneous Transluminal Coronary Angioplasty and Its Impact on Related Cardiovascular Markets.

*Primary Examiner*—Beverly M. Flanagan
*Attorney, Agent, or Firm*—Donald E. Stout

[57] ABSTRACT

A method of viewing an interior passage of a patient using an endoscope and a catheter which includes a catheter body having a distal end and a lumen opening at the distal end and a displacing member. The method comprises advancing the catheter into the passage in the patient with the displacing member extending beyond the distal end of the catheter body when the catheter body is at a region of the passage. The endoscope is provided in the lumen of the catheter with the endoscope being movable longitudinally relative to the catheter and being at a location for viewing the interior passage. The method includes relatively displacing the distal end of the catheter body and material within or forming the passage within a zone of the interior passage utilizing the displacing member and viewing at least a portion of such zone of the interior passage utilizing the endoscope.

42 Claims, 3 Drawing Sheets

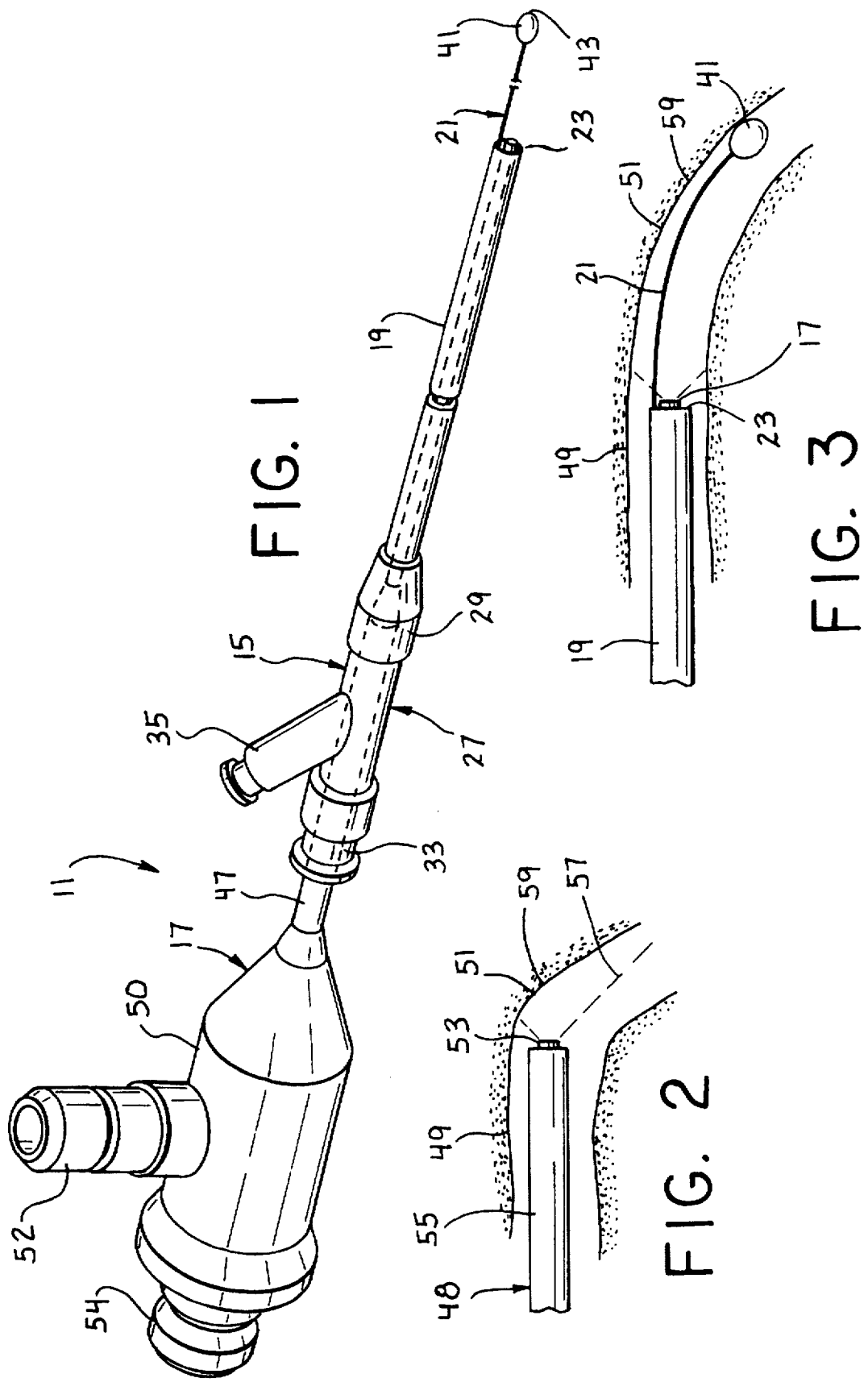

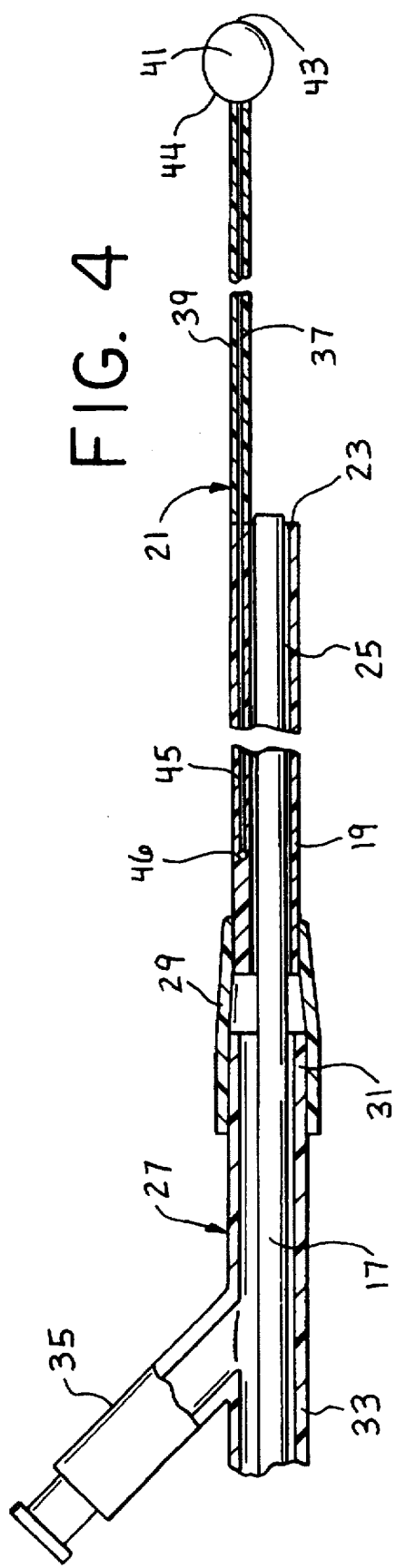
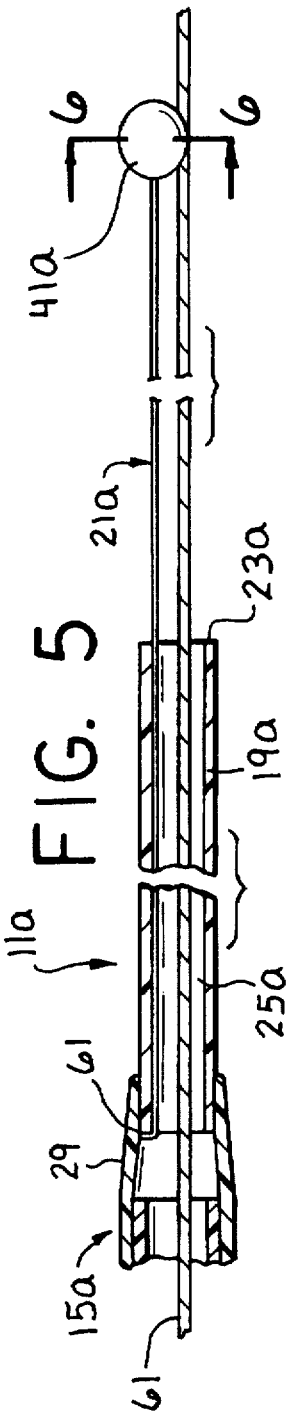
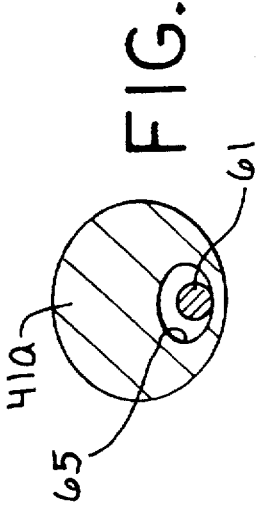
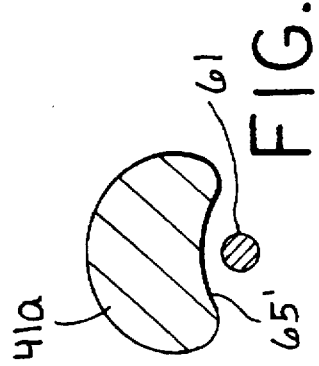

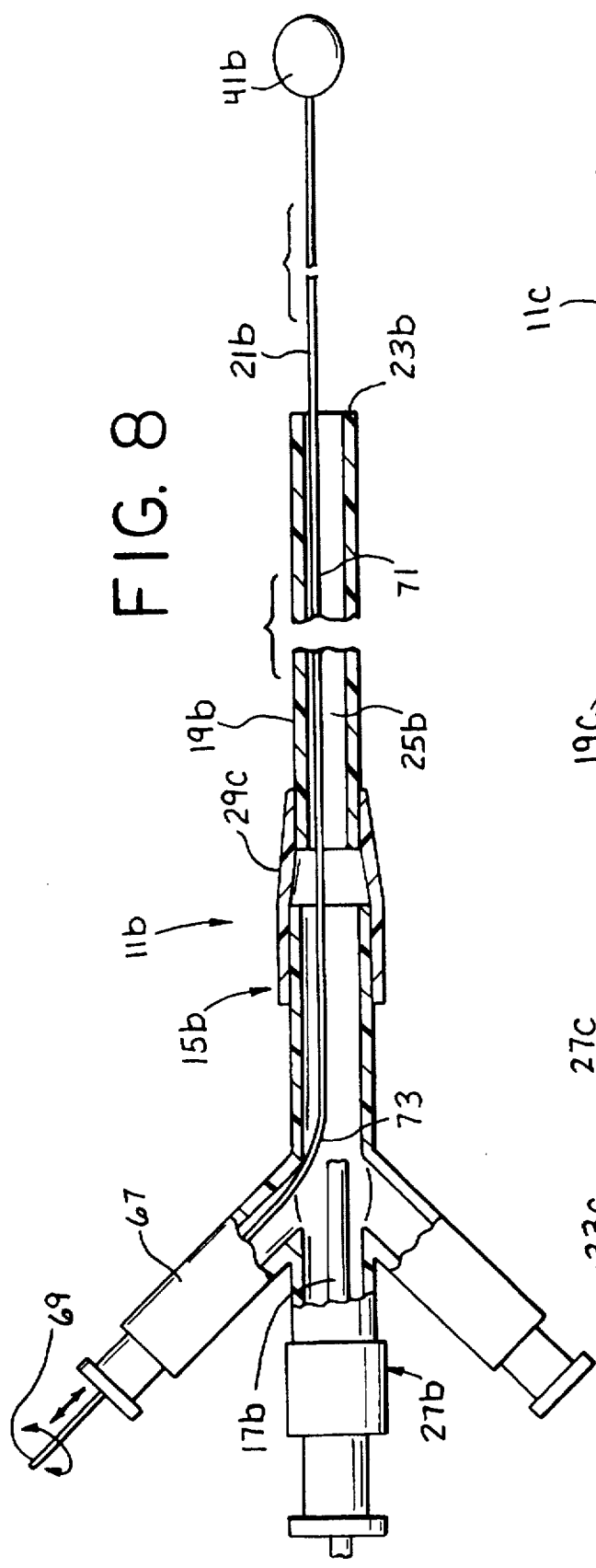
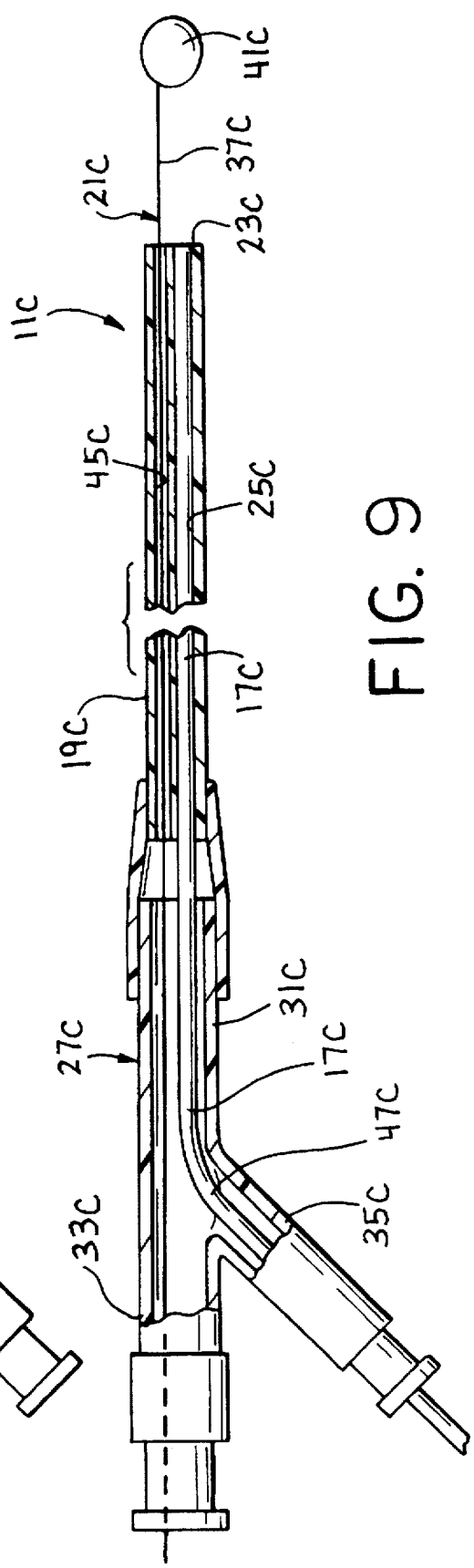

CATHETER AND ENDOSCOPE SYSTEM WITH DISTAL PROTRUDING BALL TIP AND METHOD

CROSS REFERENCE TO RELATED APPLICATION

This application is a continuation-in-part of application Ser. No. 08/238,314 filed on May 5, 1994 and entitled Endoscope With Protruding Member and Method of Utilizing the Same now U.S. Pat. No. 5,505,686 and is also related to application Ser. No. 08/630,121, filed Apr. 8, 1996, and entitled CATHETER WITH GUIDEWIRE AND ROUNDED ENLARGEMENT AND METHOD.

BACKGROUND OF THE INVENTION

Endoscopes are commonly used to view an interior passage of the body of a patient. For example, an endoscope may be used to view an interior passage such as a fallopian tube or a passage of the vascular system.

Various techniques can be used to place the endoscope at a desired location in the interior passage of the patient. For example, one such technique includes inserting a guidewire into the interior passage and running a catheter over the guidewire to approximately the desired location. With the catheter positioned in the interior passage, the guidewire may be withdrawn from the catheter and thereafter an endoscope inserted through a lumen of the catheter. Another known technique is to use a monorail system in which the endoscope is run along a prepositioned guidewire to a desired location in the interior passage. It is also known to provide an angioplasty catheter with a fixed guidewire which allows the operator to track and place the catheter at the desired location in the vascular system.

One problem with these procedures is that it may be difficult to view curved, collapsed or partially collapsed portions of the passage. In addition, material within the passage may tend to obstruct viewing through the endoscope within the field of view of the endoscope.

In an effort to solve this problem, it is known to use a resectoscope for removing or ablating unwanted tissue. It is also known to use a nozzle in an attempt to spray material off the distal lens of the endoscope as shown, for example in Auhll et al U.S. Pat. No. 5,207,213. However, these techniques do not address the visualization problems posed by a curved, collapsed or partially collapsed passage and resection increases the likelihood of injury and trauma to the patient. Similarly, the use of a technique as shown for example in Hiltebrandt U.S. Pat. No. 4,682,585 for radially spacing the distal objective of the endoscope is also not effective to address these problems.

Endoscopes have also been introduced through hollow sleeves with sharpened points for puncturing the abdomen in laparoscopic procedures such as shown in Hiltebrandt U.S. Pat. No. 4,345,589 and Yoon U.S. Pat. No. 4,254,762. However, the rigidity of the hollow sleeves and their sharp tips make them unsuited for many procedures where tissue penetration is to be avoided and for passages which are curved.

The invention of original application Ser. No. 08/238,314 now U.S. Pat. No. 5,505,686 solves these problems and enhances the viewing of the passage in which the endoscope is placed by relatively displacing the distal end of the endoscope and material within or forming the passage. According to the parent application, to accomplish the desired relative displacement the endoscope includes an elongated displacing member mounted on, and carried by, the endoscope body. This elongated displacing member can relatively displace the distal end of the endoscope body and material within the field of view of the endoscope to enhance viewing of the passage with the endoscope.

SUMMARY OF THE INVENTION

This invention enhances the view of an interior passage of a patient when the endoscope is provided in a lumen of a catheter. With this invention, it is the catheter, and not the endoscope, which carries the displacing member. The displacing member is used to relatively displace the distal end of the catheter body and material within or forming the passage within a zone of the interior passage. Consequently, viewing of at least a portion of such zone of the interior passage is facilitated.

An endoscope is relatively expensive as compared with a catheter which is used to introduce the endoscope. For this reason, endoscopes are typically sterilized and reused whereas the catheters for endoscope introduction are typically disposable. The useful life of an endoscope may be longer than the useful life of the displacing member, and the displacing member is relatively inexpensive.

One important advantage of having the displacing member carried by the catheter is that the relatively shorter useful life of the displacing member cannot reduce the longer useful life of the endoscope. Also, because the displacing member is relatively inexpensive, it does not add significantly to the cost of the disposable catheter.

A catheter useable with this invention may include a catheter body having a distal end and a lumen opening at the distal end and a displacing member which extends beyond the distal end of the catheter body at least when the catheter is at a region of the interior passage of the patient. According to one aspect of the method of this invention, the catheter body is advanced into the interior passage of the patient and an endoscope is provided along the catheter body and preferably in the lumen of the catheter body. The endoscope is movable longitudinally relative to the catheter body and is at a location for viewing the interior passage. The method also includes relatively displacing the distal end of the catheter body and material within or forming the passage within a zone of the interior passage utilizing the displacing member and viewing at least a portion of such zone of the interior passage utilizing the endoscope while the distal end of the catheter body and such material are relatively displaced.

Various techniques can be used to provide the endoscope in the lumen of the catheter. For example, with the catheter body desirably placed in the interior passage, the endoscope may be subsequently advanced into the lumen relative to the catheter body. Alternatively, the endoscope may be inserted into the lumen of the catheter body prior to placement of the catheter body in the interior passage in which event the endoscope and catheter body are advanced together in the interior passage of the patient.

The relative displacement of the distal end of the catheter body and material in or forming the passage may open a collapsed or partially collapsed passage, displace the distal end of the catheter body from the wall of the passage, displace material within the passage that would otherwise obstruct the view and/or straighten a curved portion of the interior passage. The step of relatively displacing may include moving the catheter body relative to the endoscope.

The displacing member may be fixedly mounted on the catheter body or it may be movable longitudinally relative to the catheter body. Preferably, the displacing member includes a rounded enlargement which may be at the distal end of the displacing member.

One feature of the invention is that the rounded enlargement can be used to aid the advancing movement of the catheter in the interior passage. To accomplish this, the enlargement is preferably relatively close to the distal end of the catheter body during the advancing movement of the catheter body and the displacing member and catheter body are relatively moved to move the enlargement farther distally of the distal end of the catheter body after the catheter body is advanced to or near a desired location for viewing in the interior passage. This feature of the invention is applicable whether or not the endoscope is movable relative to the catheter.

This invention also provides for advantageous cooperation between the enlargement and a guidewire used for placement of the catheter. According to this feature of the invention, while the catheter body is moved over a guidewire, the enlargement is guided over the guidewire with a longitudinally extending guiding surface of the enlargement. Thus, the guiding surface cooperates with the guidewire to tend to maintain guiding contact between the enlargement and the guidewire. This guiding surface may include, for example, a longitudinally extending recess and/or a passage extending longitudinally through the enlargement.

The displacing member can be used in essentially the same manner as described in original application Ser. No. 08/238,314, which is incorporated by reference herein. For example, if the interior passage has a curve, the displacing member may be elongated and extend beyond the distal end of the catheter body when the catheter is near the curve. In this event, the displacing member may be used to at least assist in guiding the catheter body at least part way through the curve as the catheter body is advanced in the interior passage. Thus, the displacing member may serve a catheter guiding function as well as enhancing or enlarging the view obtained from the endoscope. As to the view enhancing feature, the displacing member may be moved longitudinally relative to the catheter body and/or the entire catheter and/or endoscope may be moved to achieve the desired view within the field of view of the endoscope. In one or more forms of the invention the displacing member can be rotated relative to the catheter body and this may cause the distal end of the displacing member to sweep through an arc to enhance viewing.

The interior passage of the patient may be any of a variety of body passages. For example, the interior passage may be a fallopian tube, the gastrointestinal tract, a passage in the vascular system, a neural passage, an epidural passage or the urinary tract including the urethra and ureter.

An apparatus constructed in accordance with the teaching of this invention may include an endoscope and a catheter including an elongated catheter body adapted to be received in the interior passage and the displacing member. The catheter body has a distal end and a lumen extending to the distal end. The displacing member is carried by the catheter body and extends longitudinally beyond the distal end of the catheter body. The endoscope is positionable within the lumen of the catheter body and is movable longitudinally within the lumen relative to the catheter body for viewing a zone of the interior passage when the catheter body is within the interior passage. The displacing member is capable of contacting material within or forming the passage and relatively displacing the distal end of the catheter body and such material to facilitate viewing of such zone with the endoscope. Also, a fluid such as a drug or a contrast dye or an elongated medical instrument such as a probe (e.g. a cystology brush or pH probe) may be introduced through the lumen of the catheter body to the interior passage whether or not the endoscope is in the lumen.

A number of variations are possible. For example, the catheter body may have an auxiliary lumen and the displacing member may be received in the auxiliary lumen. The displacing member may be bonded with a bonding material in the auxiliary lumen or the displacing member may be moveable in the auxiliary lumen. Alternatively, the displacing member may extend at least part way through the lumen of the catheter.

The displacing member may include an elongated wire and a sheath, which may for example be or include a jacket or a helically wound coil, encasing the wire. One advantage of this construction is that if the wire should break during use the sheath tends to prevent the broken piece of wire from falling off into the interior passage of the patient. The sheath may increase the strength or resilience of the wire.

The displacing member is preferably resilient and the resilience allows it to be elastically deflected, and when the deflecting force is removed, its resilience, elasticity or memory will return it to its original unstressed position. At least those displacing members which are relatively long are preferably flexible in the sense that they can be elastically or resiliently deflected, but are not flexible in the sense of a length of string which has no memory for returning to its original position. Preferably, at least those displacing members which are relatively long are highly elastic so they can be very easily deflected. If the resilient member required substantial force to deflect, the risk of penetration of the wall of the passage would increase, however, this risk can be eliminated by using a displacing member which includes a rounded enlargement at the distal end of a displacing member which may be shorter or stiffer. Thus, the exposed length of the displacing member, at least for some applications, may be quite stiff.

The enlargement of the resilient member provides a relatively wide area in radial cross section. For some applications it is preferred that the enlargement have a maximum cross-sectional area which is at least about as large as the cross-sectional area of the distal end of the catheter. For medical applications in the fallopian tube, the maximum cross-sectional dimension of the enlargement is preferably between about 0.15 millimeter and 1.2 millimeters. To further reduce the likelihood of tissue penetration, a region of the resilient member proximally of the distal end of the resilient member may be made of increased flexibility. If desired, this region may be of progressively increasing flexibility as such region extends distally.

The spacing between the enlargement and the distal end of the catheter body can be selected depending upon the nature of the passage being examined. By way of example, in the fallopian tube the enlargement has a distal end which is between about 1 millimeter and 15 millimeters from the distal end of the catheter body. A spacing of between about 1 and about 6 millimeters is preferred for some applications and in one preferred embodiment this spacing is about 2 millimeters.

The invention, together with additional features and advantages thereof may best be understood by reference to the following description taken in connection with the accompanying illustrative drawings.

BRIEF DESCRIPTION OF THE DRAWINGS

FIG. 1 is a perspective view of an apparatus for viewing an interior passage of a patient.

FIGS. 2 and 3 are fragmentary, elevational views partially in section comparing the use of a prior art apparatus and the apparatus of this invention adjacent a curved region of an interior passage of a patient.

FIG. 4 is a fragmentary, longitudinal sectional view through the apparatus shown in FIG. 1.

FIG. 5 is a fragmentary, longitudinal view of a second embodiment of the invention and showing how this embodiment may be used with a guidewire.

FIG. 6 is an enlarged sectional view taken generally along lines 6—6 of FIG. 5.

FIG. 7 is a sectional view similar to FIG. 6 illustrating a further embodiment of the invention.

FIG. 8 is a longitudinal sectional view similar to FIG. 4 illustrating another embodiment of the invention.

FIG. 9 is a longitudinal sectional view illustrating another embodiment of the invention.

DESCRIPTION OF THE PREFERRED EMBODIMENTS

FIG. 1 shows an apparatus 11 constructed in accordance with the teachings of this invention which is useful in viewing an interior passage of a patient. The apparatus 11 generally includes a catheter 15, which is illustrated somewhat schematically, and an endoscope 17. The catheter 15 includes an elongated catheter body 19 (FIGS. 1 and 4) sized and adapted to be received in an interior passage of a patient and a displacing member which in this embodiment is in the form of an elongated resilient member 21. The catheter body 19 has a distal end 23 and a lumen 25 extending for the full length of the catheter body and opening at the distal end. The resilient member 21 is carried by the catheter body 19 and extends longitudinally beyond the distal end 23 of the catheter body.

The endoscope 17, which may be conventional, is positionable within the lumen 25 of the catheter body. The endoscope 17 is movable longitudinally within the lumen 25 relative to the catheter body 19 to a location for viewing a zone of the interior passage when the catheter body is within the interior passage.

The catheter 15 also includes a hub 27 suitably joined to the catheter body 19 as by a tubular connector 29. The hub 27 has a leg 31 which is coupled by the connector to the catheter body 19 and which communicates with the lumen 25 through the connector, a leg 33 which communicates with the lumen 25 and which receives the endoscope 17, and a leg 35 which also communicates with the lumen 25 and which may be used, for example, for the infusion of a fluid. The catheter body 19, the connector 29 and the hub 27 may all be constructed of a suitable polymeric material. Although the catheter body 19 may be rigid, typically it will be flexible to conform to curvatures in the interior passage of the patient. Except for the resilient member 21, the catheter 15 may be of conventional construction.

The resilient member 21 includes an elongated highly elastic strand or wire 37 (FIG. 4) which makes up substantially the full length of the resilient member and a sheath 39 encasing the wire. The resilient member 21 also includes a rounded enlargement 41 which, in this embodiment, constitutes a distal tip portion and defines a distal end 43 of the resilient member. The wire 37 makes up substantially the full length of the resilient member 21. For example, the wire 37 may be made of stainless steel or a suitable biocompatible polymeric material with sufficient flexural and column strength. In this embodiment, where high elasticity is desired, the wire 37 is constructed of a nickel-titanium alloy; however, other materials may be used if desired. The elasticity of the wire 37 makes the resilient member 21 highly flexible and easily deflected, but it will also enable the deflected resilient member to return to its natural or unstressed shape when the deflecting force is removed.

The sheath 39 is preferably constructed of Nylon, Kinar or other suitable lubricous material. The sheath 39 covers the length of the wire 37 between the distal end 23 of the catheter body 19 and the rounded enlargement 41. The sheath 39 has a thin wall and is flexible so that the resilience and elasticity of the wire 37 renders the resilient element similarly elastic and resilient. The sheath 39 is also preferably suitably bonded to the wire 37 along the full length of the wire between the distal end 23 of the catheter body 19 and the enlargement 41.

The enlargement 41 is preferably rounded so that it can be advanced through an interior passage of a patient with minimal trauma and without danger of perforation of the wall of the passage. The enlargement 41 may be a member separate from the wire 37 and attached to the wire or it may be an integrally enlarged portion of the wire. The enlargement 41 has a smoothly rounded peripheral surface 44 which is blunt or non-penetrating both proximally and at the distal end 43 so as to minimize the likelihood of penetrating tissue when the catheter body 19 is advanced or retracted within an interior passage. For example, the enlargement 41 may be spherical or generally egg-shaped and may be constructed of a polymeric material or a metal such as stainless steel or a nickel-titanium alloy.

In this embodiment, the resilient member 21 is fixed longitudinally with respect to the catheter body 19. As shown in FIG. 4, the catheter body 19 has an auxiliary lumen 45 which opens only at the distal end 23 and the resilient member is received in the auxiliary lumen. Bonding material bonds the resilient member 21 in the auxiliary lumen 45. In this embodiment, only the wire 37 extends into the auxiliary lumen 45 and the wire 37 has a proximal end with a small enlargement 46 which tends to resist pull-out of the resilient member from the auxiliary lumen 45.

The size of the enlargement 41 and its spacing from the distal end 23 of the catheter body 19 can be determined depending upon the interior passage which is to be viewed. Generally, however, the enlargement 41 has a maximum cross-sectional dimension in a radial plane of between about 0.15 and 1.2 millimeters and the enlargement is spaced between about 1 to about 15 millimeters from the distal end 23 of the catheter body 19. For spacings in the 1 to 6 millimeter range, such as about 2 millimeters, the exposed portion of the member 21 will typically be stiffer. For use in examination of a fallopian tube, the enlargement 41 preferably has a maximum cross-sectional dimension in a radial plane of about 0.6 mm and is spaced about 6 mm distally from the distal end 23 of the catheter body 19.

The endoscope 17 is preferably a fiberoptic endoscope and includes an endoscope body 47 and a hub 50. The hub has a leg 52 which can be coupled to a light source (not shown) and a leg 54 which may be coupled to an eyepiece (not shown) to permit direct visualization or for coupling to a camera (not shown) to enable an image to be viewed on a monitor. The endoscope includes illumination fibers (not shown) which extend into the leg 52 and visualization or image fibers which extend into the leg 54 in a conventional manner.

FIG. 2 shows the use of a conventional apparatus 48 being used to view the interior of a fallopian tube 49 having a curved portion 51. An endoscope 53 is delivered to a location within the fallopian tube 49 by a catheter 55 which may be an everting catheter. As shown in FIG. 2, the endoscope 53 has a field of view 57 which is obstructed by a wall 59 of the curved portion 51.

FIG. 3 illustrates the apparatus 11 of this invention delivered via a transvaginal route to the same region of the fallopian tube 49. More specifically, a guidewire (not shown) is first inserted into the fallopian tube 49 and the catheter body 19 is moved over the guidewire via the lumen 25 into about the desired location in the fallopian tube. In advancing the catheter body 19 to the position of FIG. 3, the enlargement 41 of the resilient member 21 contacts the wall 59 of the curved portion 51 and relatively displaces the distal end 23 of the catheter body and the wall 59. This relative displacement of the distal end 23 of the catheter body 19 and of the wall 59 occurs within a zone of the fallopian tube, at least a portion of which is to ultimately be viewed by the endoscope 17 while the distal end of the catheter body and such material are relatively displaced Next, the endoscope 17 is suitably provided in the lumen 25 and the endoscope is movable longitudinally relative to the catheter body 19 and can be placed at a location for viewing of the interior passage. One way to provide the endoscope 17 is to first withdraw the guidewire (not shown) from the catheter 15 and then advance the endoscope through the lumen 25 relative to the catheter body 19. Alternatively, the endoscope 17 may be placed into the lumen 25 and advanced over the guidewire along with the catheter body 19 to about the desired location in the fallopian tube 49. In any event, the endoscope 17 enables viewing at least a portion of the zone of the fallopian tube 49 while the distal end of the catheter body 43 and the wall 59 are relatively displaced.

The relative displacement of the distal end 23 and wall 59 can be accomplished in various different ways and may include moving the catheter body 19 relative to the endoscope 17. At least some of the displacement of the wall 59 relative to the distal end 23 of the catheter body 19 is in a radial direction. The contact between the enlargement 41 and wall 59 may occur during advancing and/or retracting of the catheter body 19 and/or while the catheter body is stationary within the fallopian tube 49. Because of the enlarged and rounded nature of the enlargement 41, the enlargement is unlikely to penetrate or damage the tissue of the fallopian tube. If desired, a fluid or an elongated medical instrument may be introduced through the lumen 25 before, during or after the time the endoscope is in the lumen.

FIG. 3, which is somewhat schematic in nature, may also be considered as illustrating the use of the apparatus 11 in other body passages such as the gastrointestinal tract, a passage of the vascular system, a neural passage, an epidural passage or a passage in the urinary tract such as the urethra or ureter. Also if it is desired to move the catheter body 19 through the curved portion 51, the resilient member 21 serves, in effect, as a fixed guidewire to guide the catheter body through the curved portion.

FIG. 5 shows an apparatus 11a which may be identical to the apparatus 11 in all respects not shown or described herein. Portions of the apparatus 11a corresponding to portions of the apparatus 11 are designed by corresponding reference numerals followed by the letter "a".

One difference between the apparatuses 11 and 11a is that the resilient member 21a is in the lumen 25a. Although the resilient member 21a could extend only part way through the lumen 25a in the embodiment of FIG. 5, it extends completely through the lumen 25a into the connector 29a. The resilient member can be bonded to a proximal portion of the catheter body 19a including at a proximal end 61 of the resilient member 21a. A second difference between the apparatuses 11 and 11a is that the resilient member 21a does not have the sheath 39.

FIG. 5 also shows a guidewire 63 over which the catheter 15a has been passed to place the catheter 15a in an interior passage of a patient. After the catheter body 19a has reached the desired location in the interior passage, the guidewire 61 is withdrawn and the endoscope 17 is inserted through the lumen 25a as described above. However, one additional difference between the embodiments of FIGS. 1–4 and 5 is that the rounded enlargement 41a has a guiding surface 65 (FIG. 6) for cooperation with the guidewire 61 which tends to maintain guiding contact between the enlargement 41a and the guidewire. In the form shown in FIG. 6, the guiding surface is in the form of a passage which extends longitudinally through the enlargement 41a. FIG. 7 shows an alternate guiding surface 65' in which the guiding surface forms a longitudinally extending recess in the enlargement 41a. In either event, the guiding surface cooperates with the guidewire to tend to maintain guiding contact between the enlargement 41a and the guidewire 61 as the catheter 15a is moved over the guidewire. All of the embodiments of this invention may optionally be provided with a guiding surface such as the guiding surfaces 65 and 65'.

FIG. 8 shows an apparatus 11b which is identical to the apparatus 11 in all respects not shown or described herein. Portions of the apparatus 11b corresponding to portions to the apparatus 11 are designated by corresponding reference numerals follows by the letter "b".

The catheter 15b does not have an auxiliary lumen such as the auxiliary lumen 45. Rather, the hub 27b of the catheter 15b has a leg 67 which communicates with the lumen 25b and the resilient member 21b extends through the leg 67 and the lumen 25b. The resilient member 21b has a proximal portion 69 and a distal portion 71 which extend in different directions and which are joined by a bend portion 73. With this construction, the resilient member 21b is movable longitudinally relative to the catheter body 19b and to some degree, the resilient member can be rotated about its longitudinal axis.

In use of the apparatus 11b, the catheter body may be advanced in the interior passage with the enlargement 41b relatively close to the distal end 23b of the catheter body to aid the advancing movement of the catheter body in the interior passage. For example, the resilient member 21b may be moved proximally relative to the catheter 15b from the position shown in FIG. 8 so as to place the enlargement 41b in contact with, or nearly in contact with, the distal end 23b of the catheter body 19b. The resilient member 21b may be moved to move the enlargement 41b farther distally of the distal end 23b of the catheter body 19b after the catheter body is advanced to approximately the desired location within the interior passage. In other words, when the advancing movement of the catheter body 19b is completed or essentially completed, the resilient member 21b may be moved distally relative to the catheter body 19b so as to restore the desired longitudinal or axial spacing between the enlargement 41b and the distal end 23b of the catheter body 19b.

Another feature of the embodiment of FIG. 8 is that the resilient member 21b can be moved longitudinally relative to the catheter body 19b to help achieve the desired relative displacement between the distal end 23b and material within or forming the interior passage of the patient. Also, rotational movement of the resilient member 21b relative to the catheter 15b may be used to aid in achieving the desired relative displacement to enhance viewing of the interior passage. Because of the portions 69 and 71, which extend in different directions, rotation of the resilient member 21b causes the enlargement 41b to sweep through an arc to enhance viewing.

FIG. 9 shows an apparatus 11c which is identical to the apparatus 11 in all respects not shown or described herein. Portions of the apparatus 11c corresponding to portions of the apparatus 11 are designated by corresponding reference numerals followed by the letter "c".

The catheter body 19c has an auxiliary lumen 45c which extends throughout the full length of the catheter body 19c and opens into the hub 27c. The resilient member 21c can also be moved longitudinally relative to the catheter body 19c in the same manner as described above for the apparatus 11b. The resilient member 21c is slidable longitudinally in the auxiliary lumen 45c and extends axially through the legs 31c and 33c of the hub 27c. The endoscope 17c extends through the lumen 25c and out through the leg 35c of the hub 27c. The endoscope body 47c is sufficiently flexible to allow the endoscope to curve from the leg 31c into the leg 35c.

The resilient member 21c includes the elongated wire or wire-like element 37c either with or without the sheath 39 (FIG. 4). The resilient member 21c also includes the rounded enlargement 41c which is eccentrically mounted on the wire-like element 37c. Consequently, rotation of the resilient member 21c causes the rounded enlargement 41c to sweep through an arc to aid viewing with the endoscope 17c.

Although exemplary embodiments of the invention have been shown and described, many changes, modifications and substitutions may be made by one having ordinary skill in the art without necessarily departing from the spirit and scope of this invention.

We claim:

1. A method of viewing an interior passage of a patient using an endoscope and a catheter which includes a catheter body having a distal end and a lumen opening at the distal end and a displacing member, said method comprising:

advancing the catheter into the passage in the patient with the displacing member extending beyond the distal end of the catheter body when the catheter body is at a region of the passage;

providing the endoscope in the lumen of the catheter body with the endoscope being movable longitudinally relative to the catheter body;

relatively displacing the distal end of the catheter body and material within or forming the passage within a zone of the interior passage utilizing the displacing member; and viewing at least a portion of said zone of the interior passage utilizing the endoscope while the distal end of the catheter body and said material are relatively displaced.

2. A method a defined in claim 1 wherein the step of providing includes advancing the endoscope relative to the catheter body.

3. A method as defined in claim 1 wherein the step of relatively displacing includes moving the catheter body relative to the endoscope.

4. A method as defined in claim 1 including moving the displacing member longitudinally relative to the catheter body.

5. A method as defined in claim 4 wherein the displacing member includes a rounded enlargement, said step of advancing the catheter body is carried out with the enlargement relatively close to the distal end of the catheter body to aid the advancing movement of the catheter body in the interior passage and the method includes moving the displacing member to move the enlargement farther distally of the distal end of the catheter body following the step of advancing the catheter.

6. A method as defined in claim 1 wherein the interior passage has a curve, the displacing member extends beyond the distal end of the catheter body when the catheter body is near the curve and including using the displacing member to at least assist in guiding the catheter body at least part way through the curve during the step of advancing the catheter.

7. A method as defined in claim 1 wherein the step of displacing includes moving the displacing member longitudinally relative to the catheter body.

8. A method as defined in claim 1 wherein the step of relatively displacing includes rotating the displacing member relative to the catheter body.

9. A method as defined in claim 1 wherein the interior passage is a fallopian tube.

10. A method as defined in claim 1 wherein the interior passage is the gastrointestinal tract.

11. A method as defined in claim 1 wherein the interior passage is a passage in the vascular system.

12. A method as defined in claim 1 wherein the interior passage is a neural passage.

13. A method as defined in claim 1 wherein the interior passage is an epidural passage.

14. A method as defined in claim 1 wherein the interior passage is a passage in the urinary tract.

15. A method as defined in claim 1 including introducing at least one of a fluid and an elongated medical instrument through the lumen to the interior passage.

16. A method as defined in claim 1 including carrying out said step of providing before said step of advancing.

17. A method as defined in claim 1 including carrying out said step of providing after said step of advancing.

18. A method of viewing an interior passage of a patient using a catheter which includes a catheter body having a distal end and a lumen opening at the distal end and an elongated displacing member movable longitudinally relative to the catheter body and having a rounded enlargement, said method comprising:

placing the catheter body and displacing member into the interior passage in the patient;

advancing the catheter body with the enlargement relatively close to the distal end of the catheter body to aid the advancing movement of the catheter body in the interior passage;

relatively moving the displacing member and the catheter body to move the enlargement farther distally of the distal end of the catheter body following at least a portion of the step of advancing the catheter body;

providing an endoscope in the lumen of the catheter body;

relatively displacing the distal end of the catheter body and material within or forming the passage within a zone of the interior passage utilizing the displacing member; and viewing at least a portion of said zone of the interior passage utilizing the endoscope while the distal end of the catheter body and said material are relatively displaced.

19. A method as defined in claim 18 wherein the step of advancing includes moving the catheter body over a guidewire.

20. A method as defined in claim 19 wherein the step of moving is carried out while guiding the enlargement over the guidewire with a longitudinally extending guiding surface of the enlargement.

21. A method of viewing an interior passage of a patient using an endoscope and a catheter which includes a catheter body having a distal end and a lumen opening at the distal end and a displacing member, said method comprising:

advancing the catheter into the passage in the patient with the displacing member extending beyond the distal end of the catheter body when the catheter body is at a region of the passage;

providing the endoscope along the catheter body with the endoscope being movable longitudinally relative to the catheter body;

relatively displacing the distal end of the catheter body and material within or forming the passage within a zone of the interior passage utilizing the displacing member; and viewing at least a portion of said zone of the interior passage utilizing the endoscope while the distal end of the catheter body and said material are relatively displaced.

22. A method as defined in claim 21 wherein the displacing member includes a rounded enlargement which is spaced from the distal end of the catheter body from about 1 to about 6 millimeters.

23. A method of viewing an interior passage of a patient using an endoscope and a catheter which includes a catheter body having a distal end and a lumen opening at the distal end and an elongated resilient member, said method comprising:

advancing the catheter into the passage in the patient with the resilient member extending beyond the distal end of the catheter body when the catheter body is at a region of the passage;

providing the endoscope along the catheter body with the endoscope being movable longitudinally relative to the catheter body;

relatively displacing the distal end of the catheter body and material within or forming the passage within a zone of the interior passage utilizing the resilient member; and viewing at least a portion of said zone of the interior passage utilizing the endoscope while the distal end of the catheter body and said material are relatively displaced.

24. An apparatus for viewing an interior passage of a patient comprising:

a catheter including an elongated catheter body adapted to be received in the interior passage and a displacing member, said catheter body having a distal end and a lumen extending to the distal end, said displacing member being carried by the catheter body and extending longitudinally beyond the distal end of the catheter body;

an endoscope positionable within the lumen of the catheter body, said endoscope being movable longitudinally within the lumen relative to the catheter body to a location for viewing a zone of the interior passage when the catheter body is within the interior passage; and said displacing member being capable of contacting material within or forming the passage and relatively displacing the distal end of the catheter body and such material to facilitate viewing of said zone with the endoscope.

25. An apparatus as defined in claim 24 wherein the catheter body has an auxiliary lumen and the displacing member is received in the auxiliary lumen.

26. An apparatus as defined in claim 25 including bonding material for bonding the displacing member in the auxiliary lumen.

27. An apparatus as defined in claim 25 wherein the displacing member is movable in the auxiliary lumen and includes a rounded enlargement distally of the distal end of the catheter body.

28. An apparatus as defined in claim 24 wherein the displacing member is elongated and rotatable relative to the catheter body.

29. An apparatus as defined in claim 28 wherein the displacing member has a distal end and portions extending in different directions such that rotation of the displacing member causes the distal end of the displacing member to sweep through an arc.

30. An apparatus as defined in claim 28 wherein the displacing member includes an elongated wire-like element and a rounded enlargement eccentrically mounted on the wire-like element whereby rotation of the displacing member causes the rounded enlargement to sweep through an arc.

31. An apparatus as defined in claim 24 wherein the displacing member extends at least part way through the lumen.

32. An apparatus as defined in claim 24 wherein the displacing member includes an elongated wire and a sheath encasing the wire.

33. An apparatus as defined in claim 24 wherein the displacing member includes a rounded enlargement distally of the distal end of the catheter body.

34. An apparatus as defined in claim 33 wherein the enlargement is spaced between about 1 to about 15 mm from the distal end of the catheter body and has a maximum cross-sectional dimension of between about 0.15 and 1.2 mm.

35. An apparatus as defined in claim 33 wherein the enlargement is spaced between about 1 to about 6 mm from the distal end of the catheter body.

36. An apparatus as defined in claim 33 wherein the enlargement has a guiding surface for cooperation with a guidewire which tends to maintain guiding contact between the enlargement and the guidewire.

37. An apparatus as defined in claim 33 wherein the enlargement has a longitudinally extending recess.

38. An apparatus as defined in claim 33 wherein the enlargement has a passage extending longitudinally through the enlargement.

39. An apparatus as defined in claim 24 wherein the displacing member is elongated and resilient.

40. A method as defined in claim 1 wherein the displacing member includes a rounded enlargement for use in said step of advancing.

41. A method as defined in claim 21 wherein the displacing member includes a rounded enlargement which is spaced from the distal end of the catheter body about 2 millimeters.

42. An apparatus as defined in claim 24 wherein the displacing member includes a rounded enlargement distally of the distal end of the catheter body.

* * * * *